United States Patent
Mori

(10) Patent No.: US 7,217,682 B2
(45) Date of Patent: May 15, 2007

(54) CYCLOPROPANECARBOXYLIC ACID ESTERS AND PEST CONTROLLERS CONTAINING THE SAME

(75) Inventor: Tatsuya Mori, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 417 days.

(21) Appl. No.: 10/496,992

(22) PCT Filed: Nov. 20, 2002

(86) PCT No.: PCT/JP02/12093

§ 371 (c)(1),
(2), (4) Date: May 27, 2004

(87) PCT Pub. No.: WO03/050080

PCT Pub. Date: Jun. 19, 2003

(65) Prior Publication Data

US 2005/0004389 A1    Jan. 6, 2005

(30) Foreign Application Priority Data

Dec. 11, 2001  (JP)  ............... 2001-376907
Aug. 9, 2002  (JP)  ............... 2002-232745

(51) Int. Cl.
*A01N 37/34*  (2006.01)
*C07C 255/31*  (2006.01)
(52) U.S. Cl. ............ 504/309; 558/303; 558/388; 558/406; 558/407; 560/124
(58) Field of Classification Search ............... 558/303, 558/388, 404, 406, 407; 560/124; 504/309
See application file for complete search history.

(56) References Cited

U.S. PATENT DOCUMENTS 4,556,666 A * 12/1985 Tessier et al. ............... 514/351
4,879,302 A * 11/1989 Tessier et al. ............... 514/351
4,939,172 A    7/1990 Cadiergue et al.
5,135,951 A    8/1992 Babin et al.
5,262,438 A * 11/1993 Benoit et al. ............... 514/531
6,908,945 B2 * 6/2005 Mori ........................... 514/521

FOREIGN PATENT DOCUMENTS

GB    2 268 740 A    1/1994
JP    56-063950 A    5/1981

* cited by examiner

*Primary Examiner*—Golam M. M. Shameem
(74) *Attorney, Agent, or Firm*—Akin Gump Strauss Hauer & Feld, LLP

(57) ABSTRACT

A 4-methoxymethyl-2,3,5,6-tetrafluorobenzyl 2,2-dimethyl-3-(2-cyano-3-hydrocarbyloxy-3-oxo-1-propenyl) cyclopropanecarboxylate given by the formula (1):

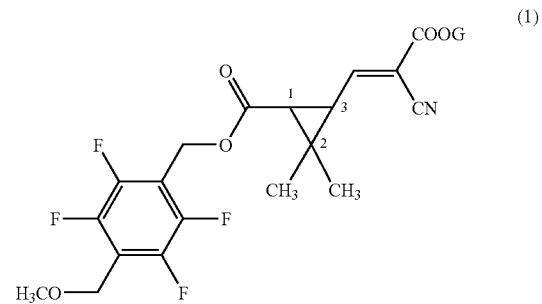

wherein G represents C1–C4 alkyl or C3–C4 alkenyl, has excellent pests controlling effect.

5 Claims, No Drawings

CYCLOPROPANECARBOXYLIC ACID ESTERS AND PEST CONTROLLERS CONTAINING THE SAME

CROSS-REFERENCE TO RELATED APPLICATIONS

This application is a section 371 of International Application No. PCT/JP03/12093, filed Nov. 20, 2003, the disclosure of which is incorporated herein by reference.

TECHNICAL FIELD OF THE INVENTION

The present invention relates to an novel cyclopropanecarboxylic acid ester and uses thereof.

BACKGROUND ART

As acid parts of natural pyrethroid compounds, two acids, one whose substituent at 3-position on the cyclopropane ring is the 2-methyl-1-propenyl and another whose substituent is 2-methyl-3-methoxy-3-oxo-1-propenyl, are known. The synthetic pyrethroid compounds, wherein the methyl at 2-position on the 2-methyl-3-methoxy-3-oxo-1-propenyl is replaced with a halogen atom, are described in U.S. Pat. No. 4,939,172, GB patent publication 2,268,740 and the like. However the pests controlling activity of these compounds is sometimes shortly, then it is desired to develop the compounds having enough activity for controlling pests.

DISCLOSURE OF THE INVENTION

The present inventor has earnestly studied for seeking the compound having excellent pests controlling activity, and found that cyclopropanecarboxylic acid esters substituted at 3-position on the cyclopropane ring with 2-cyano-3-hydrocarbyloxy-3-oxo-1-propenyl given by the following formula (1) has excellent pests controlling effect to complete the present invention.

The present invention provides 4-methoxymethyl-2,3,5,6-tetrafluorobenzyl 2,2-dimethyl-3-(2-cyano-3-hydrocarbyloxy-3-oxo-1-propenyl) cyclopropanecarboxylate (hereinafter, referred to as the present compound) given by the formula (1):

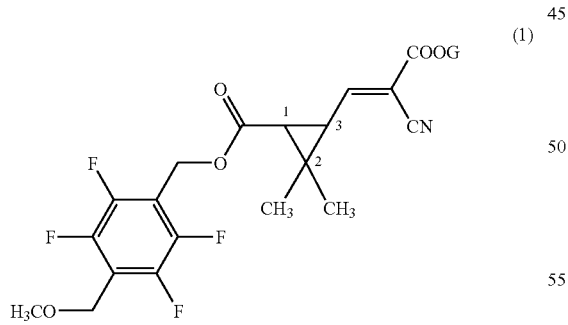

(1)

wherein G represents C1–C4 alkyl or C3–C4 alkenyl; furthermore, a pesticidal composition containing the present compound as an effective ingredient, and a method of controlling pests comprising applying an effective amount of the present compound to pests or the habitat of pests.

In the present invention, the C1–C4 alkyl represented G includes, for example, methyl, ethyl, propyl, 1-methylethyl and 1,1-dimethylethyl; the C3–C4-alkenyl includes, for example, allyl.

Embodiments for the present invention include, for example, the compound wherein the absolute configuration at 1-position on the cyclopropane ring is R-configuration in the formula (1); the compound wherein the relative configuration between the substituents at 1-position and 3-position on the cyclopropane ring is trans-configuration in the formula (1);

the compound wherein the absolute configuration at 1-position on the cyclopropane ring is R-configuration, and the relative configuration between the substituents at 1-position and 3-position on the cyclopropane ring is trans-configuration in the formula (1);

the compound wherein the absolute configuration at 1-position on the cyclopropane ring is R-configuration with 90% or more ratio in the formula (1);

the compound wherein the relative configuration between the substituents at 1-position and 3-position on the cyclopropane ring is trans-configuration with 90% or more ratio in the formula (1);

the compound wherein the absolute configuration at 1-position on the cyclopropane ring is R-configuration, and the relative configuration between the substituents at 1-position and 3-position on the cyclopropane ring is trans-configuration, with 90% or more ration in the formula (1);

the compound wherein the absolute configuration at 1-position on the cyclopropane ring is R-configuration with 80% or more ratio in the formula (1);

the compound wherein the relative configuration between the substituents at 1-position and 3-position on the cyclopropane ring is trans-configuration with 80% or more ratio in the formula (1);

the compound wherein the absolute configuration at 1-position on the cyclopropane ring is R-configuration, and the relative configuration between the substituents at 1-position and 3-position on the cyclopropane ring is trans-configuration, with 80% or more ration in the formula (1).

The present compound can be produced, for example, by making 4-methoxymethyl-2,3,5,6-tetrafluorobenzyl 2,2-dimethyl-3-formylcyclopropanecarboxylate given by the formula (2):

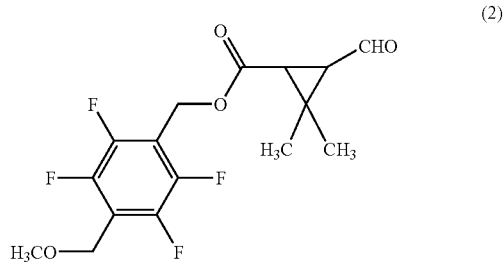

(2)

react with a cyanoacetic acid ester given by formula (3):

(3)

wherein G has the same meaning as defined above.

The reaction is usually carried out in a solvent, in the presence of a carboxylic acid salt.

The solvent utilized in the reaction includes, for example, aromatic hydrocarbons such as benzene, toluene, xylene and the like.

The carboxylic acid salt utilized in the reaction includes, for example, alkali metal salts of carboxylic acid such as sodium acetate, potassium acetate, sodium benzoate and the like, and ammonium salts of carboxylic acid such as ammonium acetate and the like.

Based on 1 mole of the compound given by the formula (2), 1 to 3 mole of the cyanoacetic acid ester given by the formula (3), and 0.1 to 2 mole of the base are usually used.

The reaction temperature for the reaction is usually within a range from room temperature to 150° C., and the reaction time is usually within a range of from 10 minutes to 24 hours.

The reaction can be carried out removing the water generated from the reaction, for example, under the condition of azeotropic dehydration.

After completion of the reaction, the present compound can be obtained by the work-up procedure such as pouring the reaction mixture into water, extracting with an organic solvent, and concentrating the organic layer; and, if necessary, the purification procedure such as chromatography and the like. The isomer of the present compound originated from the substituents on the cyclopropane ring can be produced by using the corresponding isomer of the compound given by the formula (2), and, if necessary, the purification procedure such as chromatography and the like.

The compound given by the formula (2) can be produced, for example, by making 4-methoxymethyl-2,3,5,6-tetrafluorobenzyl 2,2-dimethyl-3-(2-methyl-1-propenyl)cyclopropanecarboxylate given by the formula (4):

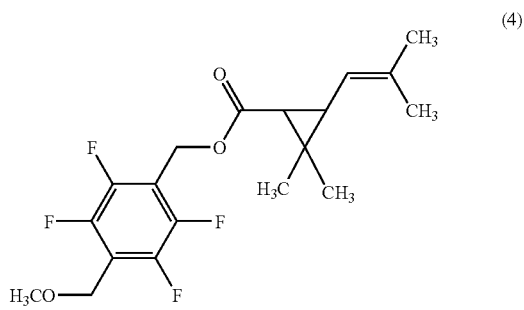

(4)

react with ozone (ozonolysis), or react with osmium tetraoxide—potassium metaperiodate.

The compound given by the formula (4) is disclosed, for example, in EP patent publication 1004569A1, and can be produced by the method described therein.

As the pests which can be controlled by the present compound, there is mentioned, example, arthropod such as insects, acarines and the like, specific examples of which are as follows:

Lepidoptera:
Pyralidae such as *Chilo suppressalis* (rice stem borer), *Cnaphalocrocis medinalis* (rice leafroller) and *Plodia interpunctella* (Indian meal moth); Noctuidae such as *Spodoptera litura* (tobacco cutworm), *Pseudaletia separata* (rice armyworm) and *Mamestra brassicae* (cabbage armyworm); Pieridae such as *Pieris rapae crucivora* (common cabbageworm); Tortricidae such as *Adoxophyes* spp.; Carposinidae; Lyonetiidae; Lymantriidae; Plusiinae; *Agrotis* spp. such as *Agrotis segetum* (turnip cutworm) and *Agrotis ipsilon* (black cutworm); *Helicoverpa* spp.; *Heliotis* spp.; *Plutella xylostella* (diamondback moth); *Parnara guttata* (rice skipper); *Tinea pellionella* (casemaking clothes moth); *Tineola bisselliella* (webbing clothes moth); and so on;

Diptera:
*Culex* spp. such as *Culex pipiens pallens* (common mosquito) and *Culex tritaeniorhynchus*; *Aedes* spp. such as *Aedes aegypti* and *Aedes albopictus*; *Anopheles* spp. such as *Anopheles sinensis*; Chironomidae (midges); Muscidae such as *Musca domestica* (housefly), *Muscina stabulans* (false stablefly) and *Fannia canicularis* (little housefly); Calliphoridae; Sarcophagidae; Anthomyiidae such as *Delia platura* (seedcorn maggot) and *Delia antiqua* (onion maggot); Tephritidae (fluit flies); Drosophilidae; Psychodidae (moth flies); Phoridae; Tabanidae; Simuliidae (black flies); Stomoxyidae; Ceratopogonidae (biting midges); and so on;

Dictyoptera:
*Blattella germanica* (German cockroach), *Periplaneta fuliginosa* (smokybrown cockroach), *Periplaneta americana* (American cockroach), *Periplaneta brunnea* (brown cockroach), *Blatta orientalis* (oriental cockroach) and so on;

Hymenoptera:
Formicidae (ants); Vespidae (hornets); Bethylidae; Tenthredinidae (sawflies) such as *Athalis rosae ruficornis* (cabbage sawfly); and so on;

Siphonaptera:
*Ctenocephalides canis* (dog flea), *Ctenocephalides felis* (cat flea), *Pulex irritans* and so on;

Anoplura:
*Pediculus humanus humanus* (body louse), *Pthirus pubis* (crab louse), *Pediculus capitis* (head louse), *Pediculus corporis* and so on;

Isoptera:
*Reticulitermes speratus*; *Coptotermes formosanus*; and so on;

Hemiptera:
Delphacidae (planthoppers) such as *Laodelphax striatellus* (small brown planthopper), *Nilaparvata lugens* (brown planthopper) and *Sogatella furcifera* (white backed rice planthopper); leafhoppers such as *Nephotettix cincticeps*, *Nephotettix virescens*; Aphididae (aphids); plant bugs; Aleyrodidae (whiteflies); scales; Tingidae (lace bugs); Psyllidae; and so on;

Coleoptera (beetles):
*Attagenus unicolor japonicus* (black carpet beetle) and *Authrenus verbasci* (varied carpet beetle); corn rootworms such as *Diabrotica virgifera* (western corn rootworm) and *Diabrotica undecimpunctata howardi* (southern corn rootworm); Scarabaeidae such as *Anomala cuprea* (cupreous chafer) and *Anomala rufocuprea* (soybeen beatle); weevils such as *Sitophilus zeamais* (maize weevil), *Lissorhoptrus oryzophilus* (ricewater weevil), ball weevil and *Callosobruchus chinensis* (adzuki bean weevil); Tenebrionidae (darkling beetles) such as *Tenebrio molitor* (yellow mealworm) and *Tribolium castaneum* (red flour beetle); Chrysomelidae (leaf beetles) such as *Oulema oryzae* (rice leaf beetle), *Phyllotreta striolata* (striped flea beetle) and *Aulacophora femoralis* (cucurbit leaf beetle); Anobiidae; *Epilachna* spp. such as *Epilachna vigintioctopunctata* (twenty-eight-spotted ladybird); *Lyctidae* (powderpost beetles); *Bostrychidae* (false powderpost beetles); *Cerambycidae; Paederus fuscipes* (robe beetle); and so on;

*Thysanoptera:*
Thrips palmi, Flankliniella occidentalis (western flower thrips), *Thrips hawaiiensis* (flower thrips) and so on;

*Orthoptera:*
*Gryllotalpidae* (mole crickets); *Acrididae* (grasshoppers); and so on;

*Acarina:*
*Dermanyssidae* such as *Dermatophagoides farinae* (American house dust mite) and *Dermatophagoides pteronyssinus; Acaridae* such as *Tyrophagus putrescentiae* (mold mite) and *Aleuroglyphus ovatus; Glycyphagidae* such as *Glycyphagus privatus, Glycyphagus domesticus* and *Glycyphagus destructor; Cheyletidae* such as *Chelacaropsis malaccensis* and *Cheyletus fortis; Tarsonemidae; Chortoglyphus* spp.; *Haplochthonius* spp.; *Tetranychidae* such as *Tetranychus urticae* (carmine spider mite), *Tetranychus kanzawai* (Kanzawa spider mite), *Panonychus citri* (citrus red mite) and *Panonychus ulmi* (European red mite); *Ixodidae* such as *Haemaphysalis longiconis*; and so on.

The pesticidal composition of the present invention may be the present compound itself, but it is usually the formulations supported the present compound on carriers.

The examples of the formulations include oil solutions, emulsifiable concentrates, wettable powders, flowable formulations (e.g. aqueous suspension, aqueous emulsion), dusts, granules, aerosols, volatile formulations by heating (e.g. mosquito-coil, mosquito-mat for electric heating, volatile formulations with absorptive wick for heating), heating fumigants (e.g. self-burning type fumigants, chemical reaction type fumigant, porous ceramic plate fumigant), non-heating volatile formulations (e.g. resin volatile formulations, impregnated paper volatile formulations), smoking formulations (e.g. fogging), ULV formulations and poisonous baits.

The formulation methods are, for example, as follows.
(1) A method for preparing the uniform mixing composition by adding the present compound into a liquid carrier and/or gaseous carrier, optionally with auxiliaries for formulation such as surfactants and the like, and mixing.
(2) A method for preparing the mixing composition by adding the present compound into powdered solid carrier, optionally with with auxiliaries for formulation such as surfactants and the like, and mixing.
(3) A method of impregnating a molded base material; or adding the present compound into powdered solid carrier, optionally with with auxiliaries for formulation such as surfactants and the like, mixing, and molding.

The content of the present compound depends on the type of formulations, but these formulations usually contain 0.001 to 95% by weight of the present compound.

Examples of the carrier to be used for the formulation include solid carriers such as clays (e.g. kaolin clay, diatomaceous earth, synthetic hydrated silicon oxide, bentonite, Fubasami clay, acid clay), talc and the like, ceramics, other inorganic minerals (e.g. sericite, quartz, sulfur, active carbon, calcium carbonate, hydrated silicon oxide, montmorillonite) and chemical fertilizers (e.g. ammonium sulfate, ammonium phosphate, ammonium nitrate, urea, ammonium chloride); liquid carriers such as water, alcohols (e.g. methanol, ethanol), ketones (e.g. acetone, methyl ethyl ketone), aromatichydrocarbons (e.g. benzene, toluene, xylene, ethylbenzene, methylnaphthalene, phenylxylylethane), aliphatic hydrocarbons (e.g. hexane, cyclohexane, kerosene, gas oil), esters (ethyl acetate, butyl acetate), nitriles (e.g. acetonitrile, isobutyronitrile), ethers (e.g. diisopropyl ether, dioxane), acid amides (e.g. N,N-dimethylformamide, N,N-dimethylacetamide), halogenated hydrocarbons (dichloromethane, trichloroethane, carbon tetrachloride), dimethyl sulfoxide, vegetable oils (e.g. soybean oil, cottonseed oil); and gaseous carriers such as flon gas, butane gas, LPG (liquefied petroleum gas), dimethyl ether and carbon dioxide.

Examples of the surfactant include alkyl sulfates, alkylsulfonate salts, alkylarylsulfonate salts, alkyl aryl ethers, polyoxyethylene compounds of alkyl aryl ethers, polyethylene glycol ethers, polyhydric alcohol esters and sugar alcohol derivatives.

Examples of the other auxiliaries for formulation include sticking agents, dispersing agents and stabilizers, typically casein, gelatin, polysaccharides (e.g. starch, gum arabic, clulose ves,alginic acid), lignin derivatives, bentonite and synthetic water-soluble polymers (e.g. polyvinyl alcohol, polyvinylpyrrolidone), polyacrylic acid, BHT (2,6-di-tert-butyl-4-methyphenol) and BHA (mixture of 2-tert-butyl-4-methoxyphenol and 3-tert-butyl-4-methoxyphenol).

An example of the solid base material of the mosquito-coil is a mixture of raw plant powder such as wood powder and *Pyrethrum marc* and a binding agent like Tabu powder (powder of *Machilus thunbergii*), starch or gluten.

An example of the molded base material of the mosquito-mat for electric heating is a plate of compacted fibrils of cotton linters or a mixture of pulp and cotton linters.

The base material of the self-burning type fumigant includes, for example, exothermic agents (e.g. nitrates, nitrites, guanidine salts, potassium chlorate, nitrocellulose, ethylcellulose, wood powder), pyrolytic stimulating agents (e.g. alkali metal salts, alkaline earth metal salts, dichromates and chromates), oxygen sources (e.g. potassium nitrate), combustion assistants (e.g. melanin, wheat starch), bulk fillers (e.g. diatomaceous earth) and binding agents (e.g. synthetic glue).

The base material of the chemical reaction type fumigant includes, for example, an exothermic agents (e.g. alkali metal sulfides, polysulfides, hydrogensufides, calcium oxide), catalytic agents (e.g. carbonaneous substances, iron carbide and activated clay), organic foaming agents (e.g. azodicarbonamide, benzenesulfonylhydrazide, dinitrosopentamethylene tetramine, polystyrene, polyurethane) and fillers (e.g. natural or synthetic fibers).

Examples of the base material of the non-heating volatile formulation include thermoplastic resins and paper (e.g. filter paper, Japanese paper).

The base material of the poisonous bait includes bait components (e.g. grain powder, vegetable oil, sugar, crystalline cellulose), antioxidants (e.g. dibutylhydroxytoluene, nordihydroguaiaretic acid), preservatives (e.g. dehydroacetic acid), substances for preventing erroneous eating from children and pets (e.g. red pepper powder), pest-attractant flavors (e.g. cheese flavor, onion flavor, peanut oil).

The method for controlling pests of the present invention is usually carried out by applying the pesticidal composition of the present invention to the pests or a place where the pests inhabit.

The application methods of the pesticidal composition of the present invention are, for example, given below. The methods are suitably selected according to the type of the pesticidal composition or application places.

(1) A method of applying the formulation as it is to pests or a place where the pests inhabit.
(2) A method of diluting the formulation with a solvent such as water, and then applying it to pests or a place where the pests inhabit.
(3) A method of vaporizing the present compound at a place where the pests inhabit with the formulation under normal temperature or heating condition.

In the case of (2), the concentration of the dilution is usually 0.1 to 10000 ppm.

The dosage of the present compound can be determined appropriately by a type of the formulation, a time of application, a place of application, a method of application, a species of pests, a damage level and so on in every case. In the case of treating plane, it is usually in a range of 1 to 10000 mg per 1 $m^2$ of the application area; and in the case of treating space, it is usually in a range of 0.1 to 5000 mg per 1 m3 of application space.

The pesticidal composition of the present invention can be used by combinatinon use or simultaneous use with the other insecticide, nematocide, soil-pest controlling agent, fungicide, herbicide, plant growth regulator, repellent, synergist, fertilizer or soil conditioner under pre-mixed conditions or non-mixed conditions.

Examples of the active ingredients of the insecticide and acaricide include organophosphorus compounds such as fenitrothion, fenthion, diazinon, chlorpyrifos, acephate, methidathion, disulfoton, DDVP, sulprofos, cyanophos, dioxabenzofos, dimethoate, phenthoate, malathion, trichlorfon, azinphos-methyl, monocrotophos and ethion; carbamate compounds such as BPMC, benfuracarb, propoxur, carbosulfan, carbaryl, methomyl, ethiofencarb, aldicarb, oxamyl and fenothiocarb; pyrethroid compounds such as etofenprox, fenvalerate, esfenvalerate, fenpropathrin, cypermethrin, permethrin, cyhalothrin, deltamethrin, cycloprothrin, fluvalinate, bifenthrin, 2-methyl-2-(4-bromodifluoromethoxyphenyl)propyl 3-phenoxybenzyl ether, tralomethrin, silafluofen, d-phenothrin, cyphenothrin, d-resmethrin, acrinathrin, cyfluthrin, tefluthrin, transfluthrin, tetramethrin, allethrin, prallethrin, empenthrin imiprothrin, d-furamethrin and 5-(2-propynyl)furfuryl 2,2,3,3-tetramethylcyclopropanecarboxylate; nitroimidazolidine derivatives; N-cyanoamidine derivatives such as N-cyano-N'-methyl-N'-(6-chloro-3-pyridylmethyl)acetoamidine; chlorinated hydrocarbons such as endosulfan, a-BHC and 1,1-bis(chlorophenyl)-2,2,2-trichloroethanol; benzoylphenylurea compounds such as chlorfluazuron, teflubenzuron and flufenoxuron; phenylpyrazole; metoxadiazon; bromopropylate; tetradifon; chinomethionat; pyridaben; fenpyroximate; diafenthiuron; tebufenpyrad; polynactins complex such as tetranactin, dinactin and trinactin; pyrimidifen; milbemectin; abamectin; ivermectin; and azadirachtin.

Examples of the repellent include 3,4-caranediol, N,N-diethyl- m-toluamide, 1-methylpropyl 2-(2-hydroxyethyl)-1-piperidinecarboxylate, p-menthan-3,8-diol and botanical essential oils (e.g. hyssop oil).

Examples of the synergist include bis(2,3,3,3-tetrachloropropyl) ether (S-421), N-(2-ethylhexyl)bicyclo[2.2.1]hept-5-ene-2,3-dicarboximide (MGK-264) and 5-[[2-(2-butoxyethoxy)ethoxy]methyl]-6-propyl-1,3-benzodiox ole (piperonyl butoxide).

The present invention is explained by production example, formulation examples, test example and so on, and the present invention is not restricted by these examples.

First, the production examples of the present compound are shown.

PRODUCTION EXAMPLE 1

Into 10 ml of benzene were dissolved 1.0 g of 4-methoxymethyl-2,3,5,6-tetrafluorobenzyl 2,2-dimethyl-3-formylcyclopropanecarboxylate produced according to the Reference Production Example below and 0.32 g of ethyl cyanoacetate, 0.2 g of ammonium acetate was added to the mixture, and the mixture was stirred for 1 hour under the condition of azeotropic dehydration with heating. The reaction mixture was cooled to room temperature, poured into water, and extracted with ethyl acetate. The organic layers were washed with water and saturated sodium chloride aqueous solution in sequence, dried over anhydrous sodium sulfate, and concentrated under reduced pressure. The obtained residue was subjected to silica gel column chromatography to obtain 0.96 g of 4-methoxymethyl-2,3,5,6-tetrafluorobenzyl 2,2-dimethyl-3-((E)-2-cyano-3-ethoxy-3-oxo-1-propenyl) cyclopropanecarboxylate (78%) (hereinafter, referred to as Present Compound 1).

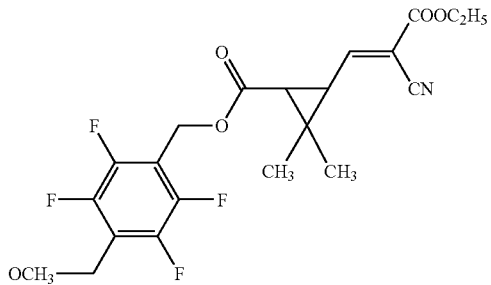

The physical property data of Present Compound 1

$^1$H-NMR (CDCl$_3$, TMS) ä (ppm): 1.32 (s, 3H), 1.34 (t, 3H), 1.40 (s, 3H), 2.08 (d, 1H), 2.65 (dd, 1H), 3.42 (s, 3H), 4.29 (q, 2H), 4.59 (s, 2H), 5.27 (s, 2H), 7.27 (d, 1H)

PRODUCTION EXAMPLE 2

Into 10 ml of benzene were dissolved 1.0 g of 4-methoxymethyl-2,3,5,6-tetrafluorobenzyl 2,2-dimethyl-3-formylcyclopropanecarboxylate produced according to the Reference Production Example below and 0.28 g of methyl cyanoacetate, 0.2 g of ammonium acetate was added to the mixture, and the mixture was stirred for 1 hour under the condition of azeotropic dehydration with heating. The reaction mixture was cooled to room temperature, poured into water, and extracted with ethyl acetate. The organic layers were washed with water and saturated sodium chloride aqueous solution in sequence, dried over sodium sulfate, and concentrated under reduced pressure. The obtained residue was subjected to silica gel column chromatography to obtain 0.71 g of 4-methoxymethyl-2,3,5,6-tetrafluorobenzyl 2,2-dimethyl-3-((E)-2-cyano-3-methoxy-3-oxo-1-propenyl) cyclopropanecarboxylate (59%) (hereinafter, referred to as Present Compound 2).

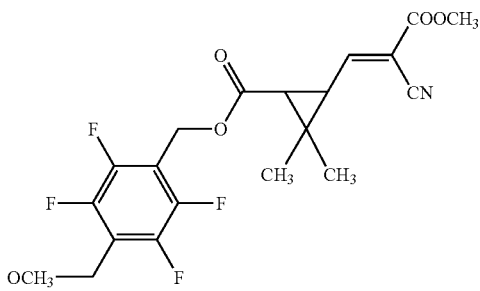

The physical property data of Present Compound 2

¹H-NMR (CDCl₃, TMS) ä (ppm): 1.30 (s, 3H), 1.39 (s, 3H), 2.07 (d, 1H), 2.65 (dd, 1H), 3.40 (s, 3H), 3.86 (s, 3H), 4.58 (s, 2H), 5.27 (s, 2H), 7.27 (d, 1H)

PRODUCTION EXAMPLE 3

By the similar method to the Production Example 1 except for using 0.36 g of propyl cyanoacetate instead of 0.32 g of ethyl cyanoacetate was obtained 0.59 g of 4-methoxymethyl-2,3,5,6-tetrafluorobenzyl 2,2-dimethyl-3-((E)-2-cyano-3-propoxy-3-oxo-1-propenyl) cyclopropanecarboxylate (hereiafter, referred to as Present Compound 3).

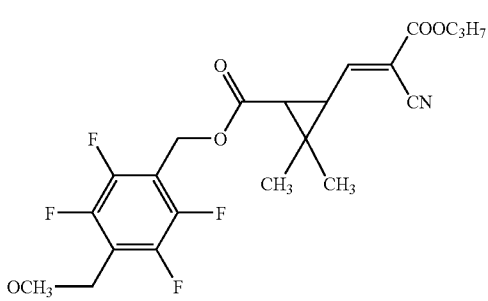

The physical property data of Present Compound 3

¹H-NMR (CDCl₃, TMS) ä (ppm): 0.96 (t, 3H), 1.32 (s, 3H), 1.39 (s, 3H), 1.75 (m, 2H), 2.08 (d, 1H), 2.65 (dd, 1H), 3.39 (s, 3H), 4.20 (t, 2H), 4.59 (s, 2H), 5.27 (s, 2H), 7.26 (d, 1H)

PRODUCTION EXAMPLE 4

By the similar method to the Production Example 1 except for using 0.36 g of allyl cyanoacetate instead of 0.32 g of ethyl cyanoacetate was obtained 0.88 g of 4-methoxymethyl-2,3,5,6-tetrafluorobenzyl 2,2-dimethyl-3-((E)-2-cyano-3-allyloxy-3-oxo-1-propenyl) cyclopropanecarboxylate (hereiafter, referred to as Present Compound 4).

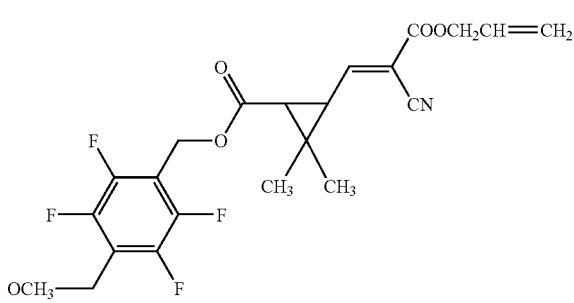

The physical property data of Present Compound 4

¹H-NMR (CDCl₃, TMS) ä (ppm): 1.32 (s, 3H), 1.39 (s, 3H), 2.09 (d, 1H), 2.66 (dd, 1H), 3.40 (s, 3H), 4.59 (s, 2H), 4.73 (d, 2H), 5.28 (s, 2H), 5.32 (dd, 2H), 5.94 (m, 1H), 7.27 (d, 1H)

PRODUCTION EXAMPLE 5

By the similar method to the Production Example 1 except for using 0.36 g of isopropyl cyanoacetate instead of 0.32 g of ethyl cyanoacetate was obtained 1.08 g of 4-methoxymethyl-2,3,5,6-tetrafluorobenzyl 2,2-dimethyl-3-((E)-2-cyano-3-isopropoxy-3-oxo-1-propenyl) cyclopropanecarboxylate (hereiafter, referred to as Present Compound 5).

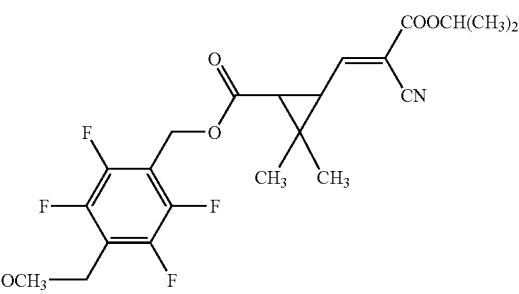

The physical property data of Present Compound 5

¹H-NMR (CDCl₃, TMS) ä (ppm): 1.30 (d, 6H), 1.32 (s, 3H), 1.40 (s, 3H), 2.12 (d, 1H), 2.65 (dd, 1H), 3.42 (s, 3H), 4.59 (s, 2H), 5.13 (m, 1H), 5.27 (s, 2H), 7.24 (d, 1H)

PRODUCTION EXAMPLE 6

By the similar method to the Production Example 1 except for using 0.40 g of t-butyl cyanoacetate instead of 0.32 g of ethyl cyanoacetate was obtained 1.15 g of 4-methoxymethyl-2,3,5,6-tetrafluorobenzyl 2,2-dimethyl-3-((E)-2-cyano-3-t-butyloxy-3-oxo-1-propenyl) cyclopropanecarboxylate (hereiafter, referred to as Present Compound 6).

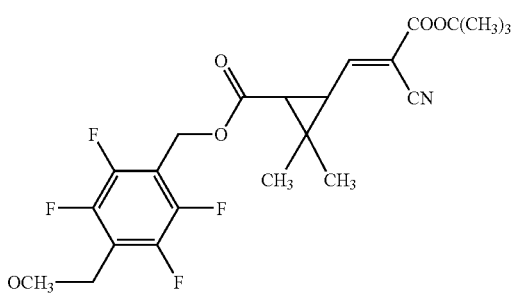

The physical property data of Present Compound 6

¹H-NMR (CDCl₃, TMS) ä (ppm): 1.30 (s, 3H), 1.41 (s, 3H), 1.52 (s, 9H), 2.06 (d, 1H), 2.64 (dd, 1H), 3.43 (s, 3H), 4.59 (s, 2H), 5.27 (s, 2H), 7.23 (d, 1H)

Next, the production example of the compound given by the formula (2) is shown as the reference example.

REFERENCE PRODUCTION EXAMPLE

Into 10 ml of tetrahydrofuran were dissolved 1.0 g of 4-methoxymethyl-2,3,5,6-tetrafluorobenzyl alcohol and 0.42 g of ethyl cyanoacetate, 0.9 g of 3-(2-methyl-1-propenyl)-2-thy-cyclopropanecarboxylic chloride {ratio of stereo isomer: (1R)-trans/(IR)-cis/(1S)-trans/(IS)-cis=93.9/2.5/3.5/0.1} was added to the mixture under ice-cooling, and the mixture was stirred for 8 hours at room temperature. The reaction mixture was poured into ice-and-water, and extracted with 80 ml of ethyl acetate twice. The organic layers were combined, washed with saturated sodium chloride aqueous solution, dried over anhydrous sodium sulfate, and concentrated under reduced pressure. The obtained residue was subjected to silica gel column chromatography to obtain 1.4 g of 4-methoxymethyl-2,3,5,6-tetrafluorobenzyl 2,2-dimethyl-3-(2-methyl-1-propenyl) cyclopropanecarboxylate given by the formula (4).

$^1$H-NMR (CDCl$_3$, TMS) ä (ppm): 1.13 (s, 3H), 1.26 (s, 3H), 1.38 (d, 1H), 1.69 (brs, 6H), 2.10 (dd, 1H), 3.40 (s, 3H), 4.59 (s, 2H), 4.87 (d, 1H), 5.24 (dd, 2H)

Into the mixture of 25 ml of tetrahydrofuran and 150 ml of 1,4-dioxane was dissolved 15.4 g of 4-methoxymethyl-2,3,5,6-tetrafluorobenzyl 2,2-dimethyl-3-(2-methyl-1-propenyl) cyclopropanecarboxylate, 1.0 g of osmium tetraoxide and 50 ml of water dissolved 24.0 g of potassium metaperiodate were added to the solution at room temperature, and the mixture was stirred for 2 hours under reflux condition. The reaction mixture was poured into about 200 ml of water, extracted with 200 ml of ethyl acetate twice. The organic layers were combined, washed with 1% sodium thiosulfate aqueous solution, saturated sodium hydrogencarbonate aqueous solution, saturated sodium chloride aqueous solution in sequence, dried over anhydrous sodium sulfaate, and concentrated under reduced pressure. The obtained residue was subjected to silica gel column chromatography to obtain 10.4 g of 4-methoxymethyl-2,3,5,6-tetrafluorobenzyl 2,2-dimethyl-3-formylcyclopropanecarboxylate given by the formula (2).

$^1$H-NMR (CDCl$_3$, TMS) ä (ppm): 1.30 (s, 3H), 1.36 (s, 3H), 2.47 (m, 2H), 3.41 (s, 3H), 4.59 (s, 2H), 5.26 (s, 2H), 9.59 (s, 1H)

Next, the formulation examples are shown. "Parts" means parts by weight.

FORMULATION EXAMPLE 1

Twenty parts of Present Compound 1 to 6 are dissolved in 65 parts of xylene. Fifteen parts of Sorpol 3005X (registered trademark of Toho Chemical) are added thereto, stirred and mixed well to give emulsifiable concentrate.

FORMULATION EXAMPLE 2

Five parts of Sorpol 3005X are added to 40 parts of Present Compound 1 to 6 and mixed well. Thirty-two parts of Carplex #80 (synthetic hydrated silica, registered trademark of Shionogi & Co.) and 23 parts of 300-mesh distomaceous earth are added thereto and mixed well with a juice mixer to give wettable powders.

FORMULATION EXAMPLE 3

A mixture of 10 parts of Present Compound 1 to 6, 10 parts of phenylxylylethane and 0.5 part of Sumidur L-75 (tolylenediisocyanate manufactured by Sumitomo Bayer Urethane Co., Ltd.) is added to 20 parts of a 10% aqueous solution of gum arabic, and stirred with a homomixer to give an emulsion having the mean particle diameter of 20 μm. Two parts of ethylene glycol are added thereto and stirred 24 hours on a water bath of 60° C. to give a microcapsule slurry. A thickening agent solution is prepared by dispersing 0.2 part of xanthan gum and 1.0 part of Beagum R (aluminum magnesium silicate manufactured by Sanyo Chemical Co., Ltd.) in 56.3 parts of ion-exchanged water. Forty-two and a half (42.5) parts of the above microcapsule slurry and 57.5 parts of the above thickening agent solution are mixed to give microencapsulated formulation.

FORMULATION EXAMPLE 4

A mixture of 10 parts of Present Compound 1 to 6 and 10 parts of phenylxylylethane is added to 20 parts of a 10% aqueous solution of polyethylene glycol and stirred with a homomixer to give an emulsion having the mean particle diameter of 3 im. Two-tenth (0.2) part of xanthan gum and 1.0 part of Beagum R (aluminum magnesium silicate manufactured by Sanyo Chemical Co., Ltd.) are dispersed in 58.8 parts of ion-exchanged water to give a thickening agent solution. Forty parts of the above emulsion and 60 parts of the above thickening agent solution are mixed to give flowable formulation.

FORMULATION EXAMPLE 5

Five parts of Present Compound 1 to 6 are mixed with 3 parts of Carplex #80 (fine powder of synthetic hydrated silicon dioxide, trademark of Shionogi & Co.), 0.3 parts of PAP (mixture of monoisopropyl phosphate and diisopropyl phosphate) and 91.7 parts of 300-mesh talc, and stirred with a juice mixer to give dusts.

FORMULATION EXAMPLE 6

One-tenth (0.1) part of Present Compound 1 to 6 is dissolved in 5 parts of dichloromethane and mixed with 94.9 parts of deodorized kerosene to give oil solution.

FORMULATION EXAMPLE 7

An aerosol vessel is filled with the solution obtained by dissolving 1 part of Present Compound 1 to 6 with 5 parts of dichloromethane and 34 parts of deodorized kerosene. The vessel is then equipped with a valve and 60 parts of propellant (liquefied petroleum gas) are charged through the valve into the aerosol vessel under pressure to give oil-based aerosol.

FORMULATION EXAMPLE 8

An aerosol vessel is filled with 50 parts of water and a mixture of 0.6 part of Present Compound 1 to 6, 5 parts of xylene, 3.4 parts of deodorized kerosene and 1 part of Atmos 300 (emulsifier, trademark of Atlas Chemical Co.). The vessel is then equipped with a valve and 40 parts of propellant (liquefied petroleum gas) is charged through the valve into the aerosol vessel under pressure to give water-based aerosol.

FORMULATION EXAMPLE 9

A solution prepared by dissolving 0.3 g of Present Compound 1 to 6 in 20 ml of acetone is homogeneously mixed with 99.7 g of a carrier for a mosquito-coil (mixture of Tabu powder, Pyrethrum marc and wood powder at the ratio of 4:3:3). After 100 ml of water is added, the mixture is kneaded well, molded and dried to give mosquito-coil.

FORMULATION EXAMPLE 10

Ten milliliters (10 ml) of solution is prepared by dissolving 0.8 g of Present Compound 1 to 6 and 0.4 g of piperonyl butoxide in acetone. 0.5 ml of the obtained solution is impregnated with a base material (a plate of compacted fibrils of a mixture of pulp ahd cotton linter: 2.5 cm×1.5 cm×0.3 cm of thichness) homogeneously to give mosquito-mat.

FORMULATION EXAMPLE 11

Three parts of Present Compound 1 to 6 is dissolved in 97 parts of deodorized kerosene. The obtained solution is charged in a vessel of polyvinyl chloride. In the vessel is inserted a porous absorptive wick which is inorganic powder solidified with a binder and then calcined, the upper portion of which wick can be heated with a heater, to give a part of an electric heating fumigation device.

FORMULATION EXAMPLE 12

A solution prepared by dissolving 100 mg of Present Compound 1 to 6 in an appropriate amount of acetone is impregnated with a porous ceramic plate (4.0 cm×4.0 cm×1.2 cm of thickness) to give fumigant for heating.

FORMULATION EXAMPLE 13

A solution prepared by dissolving 100 ig of Present Compound 1 to 6 in an appropriate amount of acetone is applied onto filter paper (2.0 cm×2.0 cm×0.3 mm of thickness) and the acetone is vaporized to give volatile agent for using at room temperature.

FROMULATION EXAMPLE 14

A acetone solution of Present Compound 1 to 6 is impregnated with a test sheet to be 1 g of the present compound per 1 m$^2$, and the acetone is vaporized to give an acaricidal sheet.

Next, the following test example shows that present compound is useful as an active ingredient of a pesticidal composition.

TEST EXAMPLE 1

A solution of 0.025 part of Present Compound 1 to 6 dissolved with 10 parts of dichloromethane was mixed with 89.9975 parts of deodorized kerosene to give a 0.025% oil solution.

Adult houseflies (5 males and 5 females) were left in a cubic chamber (70 cm at side). Seven-tenths (0.7) ml of the 0.025% oil solution of Present Compound 1 to 6 prepared above was sprayed with a spray gun at a pressure of $8.8 \times 10^4$ Pa from a small window on the side of the chamber. Then, the number of the knocked-down insects was counted at times for 10 minutes. The time for knocking down half of the tested insects ($KT_{50}$) was calculated from the result.

Furthermore, the test was similarly done by using (4-methoxymethyl-2,3,5,6-tetrafluoro)phenylmethyl [1R[1α, 3β(Z)]]-2,2-dimethyl-3-(2-fluoro-3-methoxy-3-oxopropenyl)cyclopropanecarboxylate (hereinafter, referred to as Comparative Compound):

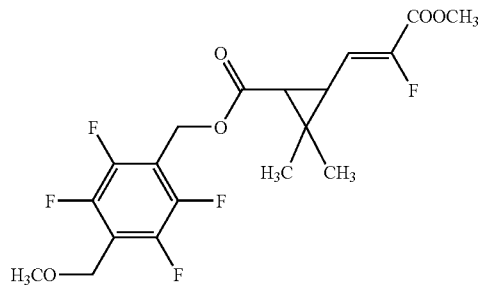

described in GB patent publication 2,268,740 as a comparative compound. The tests were done twice repeat, and the $KT_{50}$ values were calculated from the averages.

The results are shown in Table 1.

TABLE 1

| Testing compounds | $KT_{50}$ (minutes) |
| --- | --- |
| Present Compound 1 | 1.5 |
| Present Compound 2 | 1.9 |
| Present Compound 3 | 4.1 |
| Present Compound 4 | 4.3 |
| Present Compound 5 | 1.5 |
| Present Compound 6 | 3.4 |
| Comparative Compound | >10 |

INDUSTRIAL APPLICABILITY

By using the present compounds, pests can be controlled.

The invention claimed is:

1. A 4-methoxymethyl-2,3,5,6-tetrafluorobenzyl2,2-dimethyl-3-(2-cyano-3-hydrocarbyloxy-3-oxo-1-propenyl)cyclopropanecarboxylate given by the formula (1):

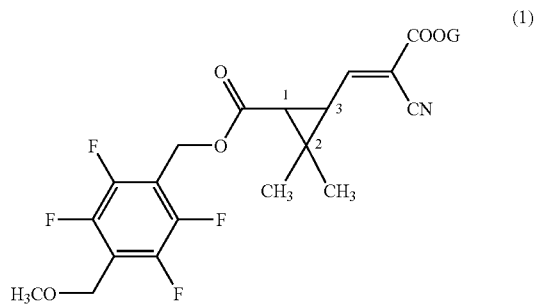

wherein G represents C1–C4 alkyl or C3–C4 alkenyl.

2. The 4-methoxymethyl-2,3,5,6-tetrafluorobenzyl 2,2-dimethyl-3-(2-cyano-3-hydrocarbyloxy-3-oxo-1-propenyl)cyclopropanecarboxylate according to claim 1, wherein the relative configuration between the substituents at 1-position and 3-position on the cyclopropane ring is trans-configuration with 80% or more ratio in the formula (1).

3. The 4-methoxymethyl-2,3,5,6-tetrafluorobenzyl 2,2-dimethyl-3-(2-cyano-3-hydrocarbyloxy-3-oxo-1-propenyl)cyclopropanecarboxylate according to claim 1, wherein the relative configuration between the substituents at 1-position and 3-position on the cyclopropane ring is trans-configuration in the formula (1).

4. A pesticidal composition containing an effective amount of the 4-methoxymethyl-2,3,5,6-tetrafluorobenzyl 2,2-dimethyl-3-(2-cyano-3-hydrocarbyloxy-3-oxo-1-propenyl) cyclopropanecarboxylate given by the formula (1):

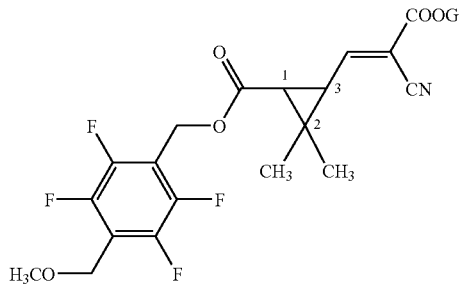

wherein G represents C1–C4 alkyl or C3–C4 alkenyl.

5. A method of controlling pests comprising applying an effective amount of the 4-methoxymethyl-2,3,5,6-tetrafluorobenzyl 2,2-dimethyl-3-(2-cyano-3-hydrocarbyloxy-3-oxo-1-propenyl) cyclopropanecarboxylate given by the formula (1) to pests or the habitat of the pests:

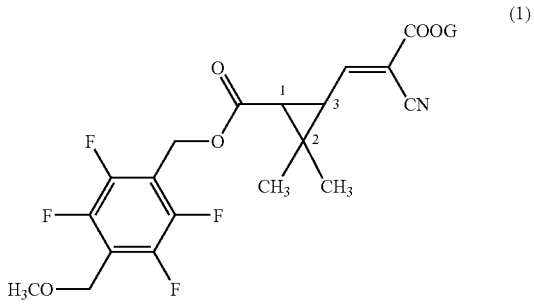

wherein G represents C1–C4 alkyl or C3–C4 alkenyl.

* * * * *